(12) United States Patent
Sieburth et al.

(10) Patent No.: US 8,987,493 B2
(45) Date of Patent: Mar. 24, 2015

(54) PROCESS FOR SYNTHESIS OF SILANE DIPEPTIDE ANALOGS

(75) Inventors: Scott McNeill Sieburth, Norwood, PA (US); Yingjian Bo, Elkins Park, PA (US)

(73) Assignee: Temple University—of the Commonwealth System of Higher Education, Philadelphia, PA (US)

( * ) Notice: Subject to any disclaimer, the term of this patent is extended or adjusted under 35 U.S.C. 154(b) by 314 days.

(21) Appl. No.: 13/698,605

(22) PCT Filed: May 20, 2011

(86) PCT No.: PCT/US2011/037352
§ 371 (c)(1),
(2), (4) Date: Nov. 16, 2012

(87) PCT Pub. No.: WO2011/146842
PCT Pub. Date: Nov. 24, 2011

(65) Prior Publication Data
US 2013/0096335 A1     Apr. 18, 2013

Related U.S. Application Data

(60) Provisional application No. 61/346,516, filed on May 20, 2010.

(51) Int. Cl.
*C07F 7/10* (2006.01)
*C07F 7/08* (2006.01)

(52) U.S. Cl.
CPC .............. *C07F 7/0827* (2013.01); *C07F 7/0818* (2013.01)
USPC ........................................................ 556/422

(58) Field of Classification Search
CPC .................................................. C07F 7/0892
USPC ........................................................ 556/422
See application file for complete search history.

(56) References Cited

U.S. PATENT DOCUMENTS

2003/0096793 A1     5/2003 Sieburth et al. ................. 514/63

OTHER PUBLICATIONS

Alonso et al., Tetrahedron, 1997, 53(42):14355-14368.*
Alonso, et al., "Reductive Deprotection of Allyl, Benzyl and Sulfonyl Substituted Alcohols, Amines and Amides Using a Naphthalene-Catalysed Lithiation", *Tetrahedron*, vol. 53, No. 42, pp. 143355-14368, 1997.
Behloul, et al., "Desilylation procedure via a naphthalene-catalysed lithiation reaction", *Tetrahedron* 61 (2005) 6908-6915.
Benkeser, et al., "The Formation of Arylsilylpotassium Compounds", *Contribution from the Chemical Laboratories of Purdue University*, received Aug. 9, 1951.
Harloff, et al., "Reactions of trimethylsiloxychlorosilanes with lithium metal—On the mechanism of the formation of trimethylsiloxysilyllithium compounds LiSiRR' (OSime$_3$)", *Journal of Organometallic Chemistry*, vol. 693, Issue 7, Apr. 1, 2008, pp. 1283-1291.
Hernandez, et al., "Further Studies toward the Stereocontrolled Synthesis of Silicon-Containing Peptide Mimics", *J. Org. Chem.*, 2010, 75, 3283-3293.
Nielsen, et al., "Stereocontrolled Synthesis of Methyl Silanediol Peptide Mimics", *J. Org. Chem.* 2007, 72, 10035-10044.
Nielsen, et al., "Sequential C—Si Bond Formations from Diphenylsilane: Application to Silanediol Peptide Isostere Precursors", *J. Am. Chem. Soc.* 2008, 130, 13145-13151.
Mudryk, et al., "Synthetically useful dianions via reductive lithiation of tetrahydrofurans by aromatic radical anions", *J. Am. Chem. Soc.* 1991, 113(5), pp. 1866-1867.
Suginome, "Bis-silylation of Unsaturated Compounds Catalyzed by Palladium-Isocyanide Complex", Doctoral Thesis, Kyoto University, Mar. 23, 1993, pp. 1-116, Scheme IV—p. 57, downloaded from http://repository.kulib.kyoto-u.ac.jp/dspace/bitstream/2433/74624/1/D_Suginome_Michinori.pdf.
Tamao, et al., "Recent developments in silicon interelement linkage: the case of Functionalized silyllithium, silylenoid and sila-ylide", *Pure Appl. Chem.*, vol. 71, No. 3, pp. 393-400, 1999.

* cited by examiner

*Primary Examiner* — Porfirio Nazario Gonzalez
*Assistant Examiner* — Kofi Adzamli
(74) *Attorney, Agent, or Firm* — Drinker Biddle & Reath LLP

(57) ABSTRACT

The invention provides a method of preparing silane dipeptide analogs, comprising the steps of treating a solution of a substituted 1,2-oxasilolane with lithium metal to form a solution of the dilithium salt of a substituted 3-hydroxypropylsilanol, and reacting the solution of the dilithium salt of the substituted 3-hydroxypropylsilanol with a substituted enamine.

20 Claims, 2 Drawing Sheets

PROCESS FOR SYNTHESIS OF SILANE DIPEPTIDE ANALOGS

CROSS-REFERENCE TO RELATED APPLICATION

This application claims the benefit of U.S. Provisional Application Ser. No. 61/346,516 filed May 20, 2010, the entire disclosure of which is incorporated herein by reference.

REFERENCE TO GOVERNMENT GRANT

The invention was made with Government support under grant number R01 GM076471 awarded by the National Institutes of Health (NIH). The Government may have certain rights in the invention.

FIELD OF INVENTION

The invention relates to a method of preparing silane dipeptide analogs useful as protease inhibitors.

BACKGROUND OF THE INVENTION

Protease inhibitors inhibit proteases, which are proteins responsible for hydrolyzing peptides or proteins into their carboxylic acid and amine components. Protease inhibitors have been used to prevent or treat viral infections, including HIV and Hepatitis C, both of which require protease activity for the infection process. In the case of HIV, protease inhibitors prevent replication by inhibiting the activity of HIV-1 protease, a viral enzyme that cleaves nascent proteins for final assembly of new virions.

Protease inhibitors have been developed or are presently undergoing testing for treating various viral infections, such as HIV infections. Examples of anti-HIV protease inhibitors are saquinavir (Fortovase™, Invirase™, Hoffman-La Roche), ritonavir (Norvir™, Abbott), indinavir (Crixivan™, Merck), nelfinavir (Viracept™, Agouron), amprenavir (Agenerase™, GlaxoSmithKline), lopinavir (Kaletra™, Abbott), atazanavir (Reyataz™, Bristol-Myers Squibb), fosamprenavir (Lexiva™, Telzir™, GlaxoSmithKline), tipranavir (Aptivus™, Boehringer-Ingelheim) and darunavir (Prezista™, Tibotec). Examples of protease inhibitors experimentally used for hepatitis C treatment are BILN 2061 (Bohringer Ingleheim), VX 950 (Telaprevir™, Vertex and Johnson & Johnson), and SCH 503034 (Schering-Plough).

Researchers are further investigating the use of anti-HIV protease inhibitors as anti-protozoals for use against malaria and gastrointestinal protozoal infections. A combination of ritonavir and lopinavir was found to have some effectiveness against Giardia infection (Dunn et al., 2007, Int. J. Antimicrob. Agents 29(1): 98-102). The drugs saquinavir, ritonavir, and lopinavir have been found to have anti-malarial properties (Andrews et al., 2006, Antimicrob. Agents Chemother. 50(2):639-48). A cysteine protease inhibitor drug was found to cure Chagas's disease in mice (Doyle et al., 207, Antimicrob. Agents Chemother. 51(11):3932).

Protease inhibitors have been further evaluated in the treatment of cancer. For example, nelfinavir and atazanavir are able to kill tumor cells in culture (Gills et al., 2007, Clin. Cancer Res. 13(17):5183-94; Pyrko et al., Cancer Res. 67(22):10920-28). Proteasome inhibitors, such as Velcade™, are now front-line drugs for the treatment of various cancers, notably multiple myeloma.

Due to the great interest in protease inhibitors, effort has been devoted to the design and synthesis of novel scaffolds that combine protease inhibition capability and good developability properties. One such novel class of compounds is the silanediol-based dipeptide analogs, such as (1). The structure of (1) mimics the structure of the hydrated carbonyl compound (2), which is an intermediate of the hydrolysis reaction of a peptide to the carboxylic acid fragment (3) and amine fragment (4). As a structural mimic of (2), compound (1) binds to the protease active site and inhibits its activity.

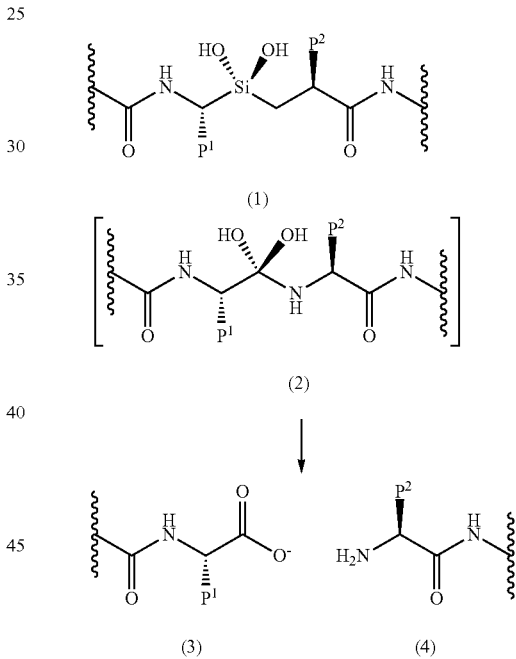

Compounds such as (1) have been prepared by a process involving approximately 15 steps, which is far too long a synthetic route to be practical. The final step of the synthesis is treatment of diphenylsilane (5) with acid, whereby a silanediol (1) is formed. Compound (5) could in principle be prepared by a condensation reaction analogous to the addition of a silyl anion (8) to a sulfinimine (7) (Nielsen & Skrydstrup, 2008, J. Am. Chem. Soc. 130:13145-51). Silyl anion (8) may be formed by treating a chlorosilane (9) with lithium metal or a lithium salt. Chlorosilanes are cheap and readily available but are extremely moisture sensitive and fume when exposed to air. Less commonly, a proteosilane (10) is used as a precursor to (8). Proteosilane (10) is easier to manipulate but is generally prepared from a moisture-sensitive chlorosilane.

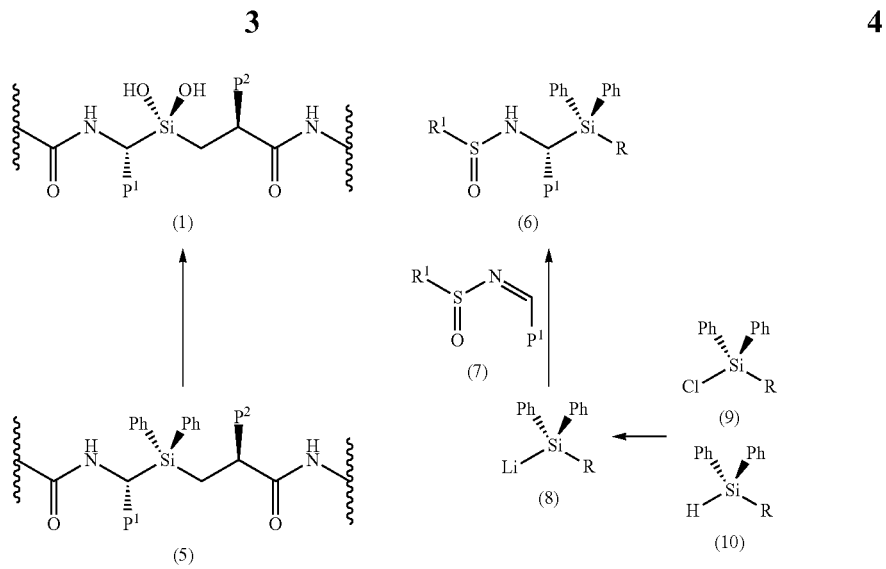

Due to the strength of the Si—O bond in a siloxy compound, its conversion to a silyl metal derivative is largely unexplored in the chemical literature. An early report described the conversion of triphenylsiloxyethane to triphenylsilyl sodium using sodium-potassium alloy in 40% yield (Benkeser et al., 1952, J. Am. Chem. Soc. 74:648-50). This report did not use substrates containing fewer than three phenyl groups attached to the silicon atom. A more recent report described the conversion of 1-dimethylphenylsiloxydecane to 1-decanol via treatment with lithium naphthalide, followed by acidic hydrolysis (Alonso et al., 1997, Tetrahedron 53:14355-68). This report did not describe the fate of the silicon group, and the synthetic protocol was rather cumbersome and difficult to scale up (Behloul et al., 2005, Tetrahedron 61:6908-15).

There is thus a need for the development of a novel synthetic methodology that allows for the efficient and convenient synthesis of a silanediol-based dipeptide analog such as (1). The synthetic methodology should allow for the synthesis of targeted compounds from commercially available and inexpensive compounds that are easy to handle. The present invention addresses and meets these needs.

SUMMARY OF THE INVENTION

The present invention relates to the unexpected discovery that a substituted 1,2-oxasilolane may be efficiently converted to the dilithium salt of a substituted 3-hydroxypropylsilanol using lithium metal, which reductively cleaves the Si—O bond in high yields. The substituted 1,2-oxasilolane starting material is easy to prepare and purify and does not present the same handling problems as chlorosilanes, which have been previously utilized in the synthesis of silyl lithium compounds. The dilithium salt of the 3-hydroxypropylsilanol may be reacted with various nucleophiles. The chemistry disclosed herein may be used to synthesize a silanediol-based dipeptide analog of formula (1) in high yield and in fewer synthetic steps than previously reported.

The invention includes a process for preparing a compound of formula (15):

wherein:
R$^1$, R$^2$ and R$^3$ are independently selected from the group consisting of H, C$_{1-10}$ alkyl, substituted C$_{1-10}$ alkyl, C$_{1-10}$ alkenyl, substituted C$_{1-10}$ alkenyl, heteroalkyl, heteroalkenyl, heterocyclyl, substituted heterocyclyl, aryl, substituted aryl, aryl-(C$_{1-3}$)alkyl, substituted aryl-(C$_{1-3}$) alkyl, formyl, alkyl-carbonyl, aryl-carbonyl, and heteroaryl-carbonyl; and, R$^4$ and R$^5$ are independently selected from the group consisting of aryl, substituted aryl, heteroaryl and substituted heteroaryl, the process comprising the step of reacting lithium metal with a compound of formula (11):

to form the compound of formula (15).

In one embodiment, the reaction is conducted in a solvent comprising tetrahydrofuran, diethyl ether or 1,4-dioxane. In another embodiment, the reaction is run at about 0° C. In yet another embodiment, R$^2$ and R$^3$ are H. In yet another embodiment, R$^1$ is methyl. In yet another embodiment, R$^4$ and R$^5$ are phenyl. In yet another embodiment, the compound of formula (11) is (S)-4-methyl-2,2-diphenyl-1,2-oxasilolane.

The invention further includes a process for preparing a compound of formula (17):

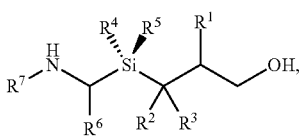

wherein:
- $R^1$, $R^2$ and $R^3$ are independently selected from the group consisting of H, $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, substituted aryl-$(C_{1-3})$alkyl, formyl, alkyl-carbonyl, aryl-carbonyl, and heteroaryl-carbonyl;
- $R^4$ and $R^5$ are independently selected from the group consisting of aryl, substituted aryl, heteroaryl and substituted heteroaryl,
- $R^7$ is $-S(O)R^8$, $-S(O)_2R^8$, $-S(O)_2NR^9R^{10}$, $-C(O)R^9$, $-C(O)NR^9R^{10}$, a protected carboxyl-linked amino acid or a protected carboxyl-linked peptide;
- $R^6$, $R^9$ and $R^{10}$ are independently selected from the group consisting of H, $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, and substituted aryl-$(C_{1-3})$alkyl; and,
- $R^8$ is $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, or substituted aryl-$(C_{1-3})$alkyl;

the process comprising the steps of:
(a) reacting lithium metal with a compound of formula (11):

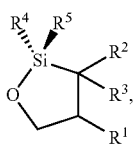

to form a compound of formula (15):

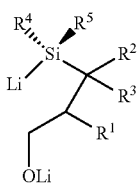

(b) reacting the compound of formula (15) with a compound of formula (16):

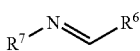

to form a reaction mixture; and,
(c) neutralizing the reaction mixture to form the compound of formula (17).

In one embodiment, the reaction in step (a) is conducted in a solvent comprising tetrahydrofuran, diethyl ether or 1,4-dioxane. In another embodiment, $R^2$ and $R^3$ are H. In yet another embodiment, $R^1$ is methyl. In yet another embodiment, $R^4$ and $R^5$ are phenyl. In yet another embodiment, the compound of formula (11) is (S)-4-methyl-2,2-diphenyl-1,2-oxasilolane. In yet another embodiment, $R^7$ is p-methylphenyl-sulfinyl.

The invention further includes a process for preparing a compound of formula (19):

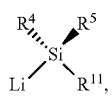

wherein:
- $R^{11}$ is $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, substituted aryl-$(C_{1-3})$alkyl, formyl, alkyl-carbonyl, aryl-carbonyl, or heteroaryl-carbonyl; and,
- $R^4$ and $R^5$ are independently selected from the group consisting of aryl, substituted aryl, heteroaryl and substituted heteroaryl;

the process comprising the step of reacting lithium metal with a compound of formula (18):

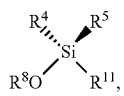

wherein:
- $R^8$ is $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, substituted aryl-$(C_{1-3})$alkyl, formyl, alkyl-carbonyl, aryl-carbonyl, or heteroaryl-carbonyl;

to form a solution of the compound of formula (19).

In one embodiment, the reaction is conducted in a solvent comprising tetrahydrofuran, diethyl ether or 1,4-dioxane. In another embodiment, the reaction is run at about 0° C. In yet another embodiment, $R^{11}$ is methyl. In yet another embodiment, $R^4$ and $R^5$ are phenyl. In yet another embodiment, the compound of formula (18) is methoxy(methyl)diphenylsilane.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DESCRIPTION OF FIGURES

Embodiments of the present invention will now be described, by way of example only, with reference to the attached Figures.

DEFINITIONS

Figure 1:
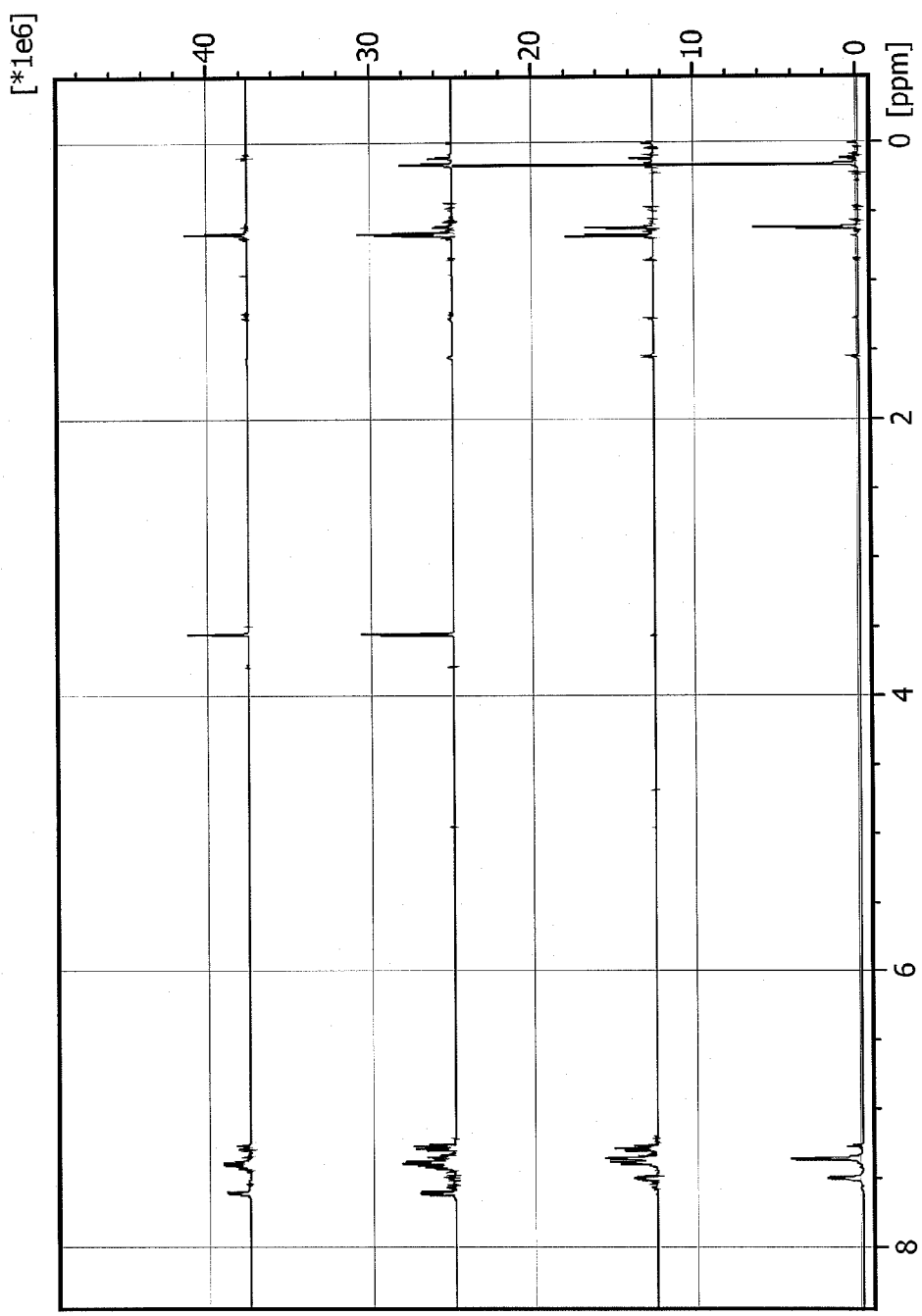
FIG. 1 shows the $^1$H NMR spectra obtained at different time points for the reaction mixture of Example 1. The spectra reproduced were acquired, from top to bottom, at 1.0 h, 1.5 h, 2.5 h and 3.5 h reaction times.
Figure 2:
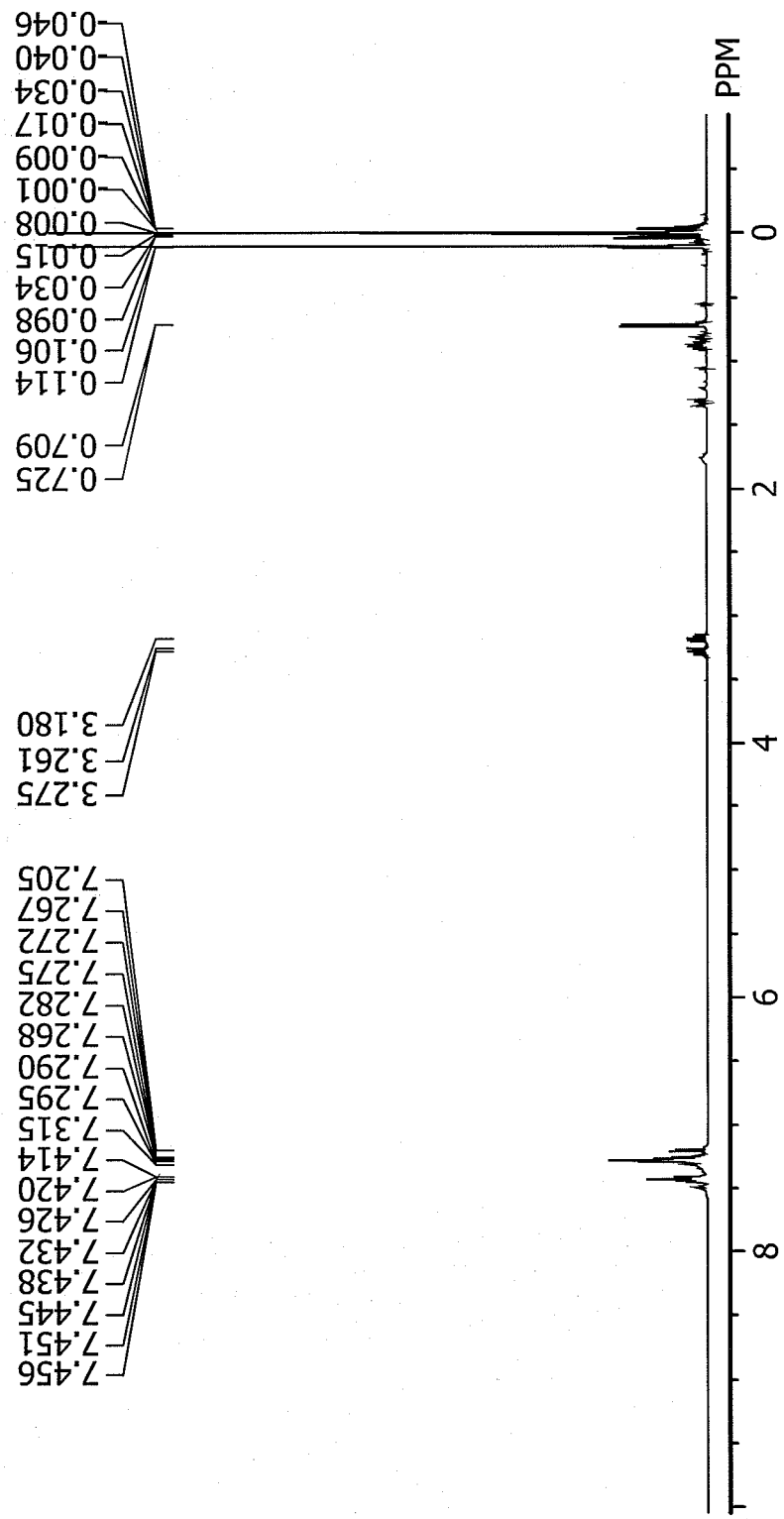
FIG. 2 shows the $^1$H NMR spectrum of compound (25).

The definitions used in this application are for illustrative purposes and do not limit the scope used in the practice of the invention.

In the following paragraphs some of the definitions include examples. The examples are intended to be illustrative, and not limiting.

Unless defined otherwise, all technical and scientific terms used herein generally have the same meaning as commonly understood by one of ordinary skill in the art to which this invention belongs. Generally, the nomenclature used herein and the laboratory procedures in analytical, organic and protein chemistries are those well known and commonly employed in the art.

As used in the specification and the appended claims, the singular forms "a," "an" and "the" include plural referents unless the context clearly dictates otherwise.

The term "about" will be understood by persons of ordinary skill in the art and will vary to some extent on the context in which it is used.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic has an N-terminus and a C-terminus. The N-terminus will have an amino group, which may be free (i.e., as a NH$_2$ group) or appropriately protected (for example, with a BOC or a Fmoc group). The C-terminus will have a carboxylic group, which may be free (i.e., as a COOH group) or appropriately protected (for example, as a benzyl or a methyl ester). A cyclic peptide does not necessarily have free N- or C-termini, since they are covalently bonded through an amide bond to form the cyclic structure. The term "peptide bond" means a covalent amide linkage formed by loss of a molecule of water between the carboxyl group of one amino acid and the amino group of a second amino acid.

The structure of amino acids and their abbreviations can be found in the chemical literature, such as in Stryer, 1988, "Biochemistry", 3rd Ed., W. H. Freeman & Co., NY, N.Y. The natural α-amino acids are alanine, arginine, asparagine, aspartic acid, cysteine, cystine, glutamic acid, glutamine, glycine, histidine, isoleucine, leucine, lysine, methionine, phenylalanine, proline, serine, threonine, tryptophan, tyrosine and valine.

As used herein, the term "carboxyl-linked amino acid" as used to describe a substituent in a molecule refers to an amino acid that is covalently bound to the molecule through the carboxyl group of the amino acid. Therefore, a "carboxyl-linked amino acid" substituent attached to an amino group indicates that the amino acid is linked through a peptide bond to the amino group. In order to facilitate the synthetic manipulation of the molecules useful within the invention, the side-chains of the carboxyl-linked amino acid may be protected with protective groups commonly used in peptide chemistry, such as Fmoc (fluorenylmethyloxycarbonyl) or tBoc (N-tert-butoxycarbonyl) for amine groups and t-butyl, methyl or benzyl esters for carboxylic groups. These groups may be deprotected according to the methods known to those skilled in the art.

Likewise, the term "carboxyl-linked peptide" as used to describe a substituent in a molecule refers to a peptide that is covalently bound to the molecule through the C-terminus carboxyl group or a side chain carboxyl group of the peptide. Therefore, a "carboxyl-linked peptide acid" substituent attached to an amino group indicates that the C-terminus carboxyl group or a side chain carboxyl group of the peptide is linked through a peptide bond to the amino group. In order to facilitate the synthetic manipulation of the molecules useful within the invention, the side-chains of the carboxyl-linked peptide may be protected with protective groups commonly used in peptide chemistry, such as Fmoc (fluorenylmethyloxycarbonyl) or tBoc (N-tert-butoxycarbonyl) for amine groups and methyl, benzyl or t-butyl esters for carboxylic groups. These groups may be deprotected according to the methods known to those skilled in the art.

As used herein, the term "alkyl", by itself or as part of another substituent means, unless otherwise stated, a straight, branched or cyclic chain hydrocarbon having the number of carbon atoms designated (i.e. $C_1$-$C_{10}$ means one to ten carbon atoms) and includes straight, branched chain or cyclic groups. Examples include methyl, ethyl, propyl, isopropyl, butyl, isobutyl, tert-butyl, pentyl, neopentyl, hexyl, cyclohexyl and cyclopropylmethyl. Most preferred is ($C_1$-$C_3$)alkyl, particularly ethyl, methyl and isopropyl.

As used herein, the term "alkenyl," employed alone or in combination with other terms, means, unless otherwise stated, a stable mono-unsaturated or di-unsaturated straight chain, branched chain or cyclic hydrocarbon group having the stated number of carbon atoms. Examples include vinyl, propenyl (allyl), crotyl, isopentenyl, butadienyl, 1,3-pentadienyl, 1,4-pentadienyl, cyclopentenyl, cyclopentadienyl and the higher homologs and isomers. A functional group representing an alkene is exemplified by —CH=CH—CH$_2$—.

As used herein, the term "substituted alkyl" or "substituted alkenyl" means alkyl or alkenyl, as defined above, substituted by one, two or three substituents selected from the group consisting of halogen, —OH, alkoxy, —NH$_2$, —N(CH$_3$)$_2$, —C(=O)OH, trifluoromethyl, —C(=O)O($C_1$-$C_4$)alkyl, —C(=O)NH$_2$, —SO$_2$NH$_2$, —C(=NH)NH$_2$, —C≡N and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

As used herein, the term "halo" or "halogen" by themselves or as part of another substituent mean, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle having one or more polyunsaturated rings having aromatic character (i.e. having (4n+2) delocalized π (pi) electrons where n is an integer).

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl($CH_2$)— and aryl(CH($CH_3$))—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarin, dihydrocoumarin, benzofuryl, particularly 3-, 4-, 1,5-naphthyridinyl, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "hydrocarbyl" refers to any moiety comprising only hydrogen and carbon atoms. Preferred hydrocarbyl groups are ($C_1$-$C_{12}$)hydrocarbyl, more preferred are ($C_1$-$C_7$)hydrocarbyl, and most preferred are benzyl and (C1-C6) alkyl.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

DETAILED DESCRIPTION OF THE INVENTION

The present invention relates to the unexpected discovery that a substituted 1,2-oxasilolane may be efficiently converted to the dilithium salt of a substituted 3-hydroxypropylsilanol using lithium metal, which reductively cleaves the Si—O bond in high yields. The dilithium salt of the 3-hydroxypropylsilanol may be reacted with various nucleophiles to form silicon-containing products.

The present invention further relates to the unexpected discovery that a substituted silyloxy compound may be efficiently converted to a silyl lithium compound using lithium metal, which reductively cleaves the Si—O bond in high yields. The silyl lithium compound may be reacted with various nucleophiles to form silicon-containing products.

Methods of the Invention

The compounds useful within the methods of the invention may be prepared by synthetic methods known to those skilled in the art of peptide and organic synthesis.

In one aspect, the 1,2-oxasilolane (11) is useful within the methods of the invention:

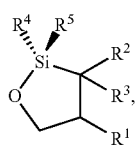

(11)

wherein:
- $R^1$, $R^2$ and $R^3$ are independently selected from the group consisting of H, $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-($C_{1-3}$)alkyl, substituted aryl-($C_{1-3}$)alkyl, formyl, alkyl-carbonyl, aryl-carbonyl, and heteroaryl-carbonyl; and
- $R^4$ and $R^5$ are independently selected from the group consisting of aryl, substituted aryl, heteroaryl and substituted heteroaryl.

Compound (11) may be prepared by methods known to those skilled in organic chemistry. In a non-limiting example, (11) may be prepared in a two-step procedure as illustrated below. The substituted allylic alcohol (12) may be reacted with the substituted chlorosilane (13) in the presence of a base, such as, but not limited to, triethylamine, diisopropylethylamine or pyridine, in an inert solvent, such as dichloromethane or tetrahydrofuran. The substituted silyloxy compound (14) may be cyclized to the corresponding substituted 1,2-oxasilolane, using in a non-limiting example a catalytic amount of rhodium (I) complexed with commercially available (S,S)-Et-ferrotane, also known as (−)-1,1'-bis[(2S,4S)-2,4-diethylphosphotano]ferrocene, as the ligand. Depending on the general substitution of (14) and the identity of the cyclization reagents the substituted 1,2-oxasilolane (11) may be obtained in high enantioselectivity.

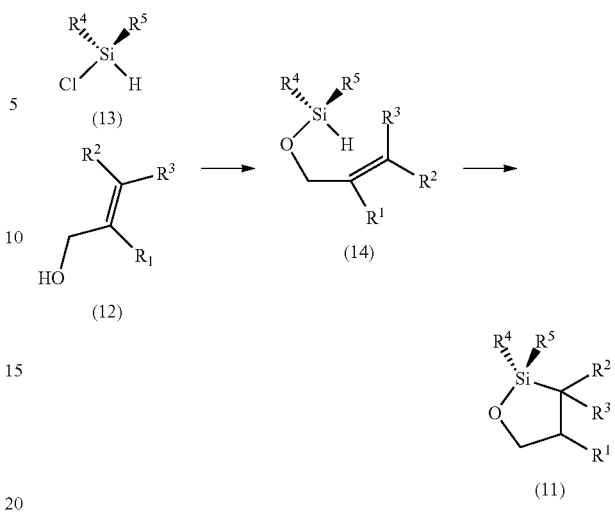

The Si—O bond in (11) may be reductively cleaved by treatment with lithium metal in an inert solvent, such as but not limited to tetrahydrofuran, diethyl ether or 1,4-dioxane. The reaction should be run under an inert atmosphere, such as argon or nitrogen gas, and under anhydrous conditions. The reaction may be run at temperatures ranging from −78° C. to room temperature. More preferably the reaction may be run at about 0° C. Ring opening in (11) yields the dilithium intermediate (15), which may be used as such in the next synthetic step.

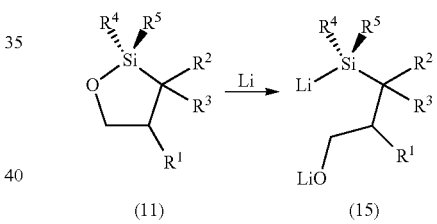

Compound (15) may be reacted with a nucleophile such as substituted enamine (16):

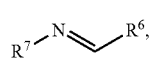

(16)

wherein:
- $R^7$ is —S(O)$R^8$, —S(O)$_2R^8$, —S(O)$_2NR^9R^{10}$, —C(O)$R^9$, —C(O)NR$^9R^{10}$, a protected carboxyl-linked amino acid or a protected carboxyl-linked peptide;
- $R^6$, $R^9$ and $R^{10}$ are independently selected from the group consisting of H, $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-($C_{1-3}$)alkyl, and substituted aryl-($C_{1-3}$)alkyl; and
- $R^8$ is $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-($C_{1-3}$)alkyl, or substituted aryl-($C_{1-3}$)alkyl;

whereby compound (17) is formed.

The reaction of compound (15) with a nucleophile should be run in an inert solvent, such as but not limited to tetrahydrofuran, diethyl ether or 1,4-dioxane. The reaction should be run under an inert atmosphere, such as argon or nitrogen gas, and under anhydrous conditions. The reaction may be run at temperatures ranging from −78° C. to 0° C. In one embodiment of the invention, the solution of (15) is added dropwise to the chilled solution of (16). In another embodiment of the invention, the solution of (16) is added dropwise to the chilled solution of (15). The reaction may be monitored by methods that are known to those skilled in the art, such as $^1$H NMR, $^{13}$C NMR, thin-layer chromatography, analytical HPLC or mass spectrometry. After the reaction is ruled to be sufficiently complete, the reaction mixture may be quenched with a mildly acidic aqueous solution, such as an ammonium chloride solution or an ammonium bisulfate solution. The desired product (17) may be isolated by methods such as silica gel chromatography, preparative chromatography, fractional crystallography or precipitation.

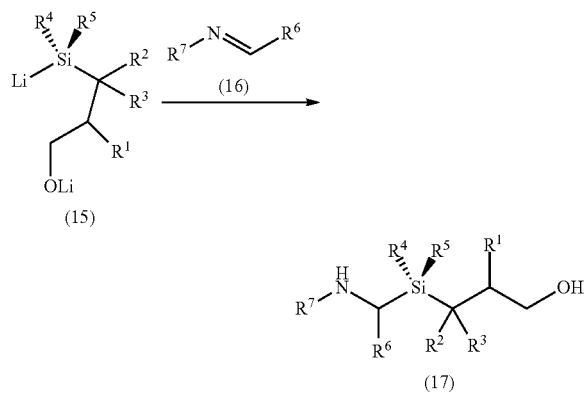

Compound (17) may be further derivatized using methods known to those skilled in the art.

In a non-limiting example contemplated within the invention, the primary alcohol in (17) may be oxidized to the corresponding carboxylic acid, using reagents such as but not limited to potassium permanganate or potassium dichromate, and coupled to amine via a peptide bond.

In another non-limiting example contemplated within the invention, the group $R^7$ may be removed using a method that preserves the integrity of the rest of the molecule. In a non-limiting example, when $R^7$ is —S(O)R$^8$, sulfinamide (17) may be hydrolyzed to the corresponding primary amine. In a non-limiting example, sulfinamines may be hydrolyzed to the corresponding amine by stirring with 4 equivalents of trifluoroacetic acid in methanol (0.25 M in methanol) at 0° C., warming to room temperature for 4 hours (Fanelli et al., "Organic Syntheses," Collected Vol. 10, pp 47-53). The resulting amine may then be coupled to a carboxylic acid via a peptide bond.

In yet another non-limiting example contemplated within the invention, groups $R^4$ and $R^5$ may be hydrolyzed to yield the corresponding silanediol. Hydrolysis of such compound may be achieved by treatment with trifluoromethanesulfonic (triflic) acid in dichloromethane at low temperature, such as 0° C.

In another aspect, the silyloxy compound (18),

wherein:
R$^8$ and R$^{11}$ are independently selected from the group consisting of $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-($C_{1-3}$)alkyl, substituted aryl-($C_{1-3}$)alkyl, formyl, alkyl-carbonyl, aryl-carbonyl, and heteroaryl-carbonyl; and,
R$^4$ and R$^5$ are independently selected from the group consisting of aryl, substituted aryl, heteroaryl and substituted heteroaryl;

may be converted to the corresponding silyl lithium compound (19) by treatment with lithium metal in an inert solvent, such as but not limited to tetrahydrofuran, diethyl ether or 1,4-dioxane. The reaction should be run under an inert atmosphere, such as argon or nitrogen gas, and under anhydrous conditions. The reaction may be run at temperatures ranging from −78° C. to room temperature. More preferably the reaction may be run at about 0° C. Compound (19) may be further reacted with nucleophiles, as appropriate.

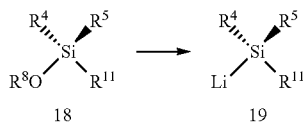

In the cases where $R^7$ in compound (16) is a protected carboxyl-linked peptide, the corresponding peptide may be synthesized de novo using peptide synthesis methods. In such methods, the peptide chain is prepared by a series of coupling reactions in which the constituent amino acids are added to the growing peptide chain in the desired sequence. The use of various N-protecting groups, e.g., the carbobenzoxy (CBZ) group or the t-butoxycarbonyl (tBoc) group; various coupling reagents e.g., dicyclohexylcarbodiimide (DCC) or carbonyldiimidazole (CDI); various active esters, e.g., esters of N-hydroxyphthalimide or N-hydroxy-succinimide; and the various cleavage reagents, e.g., trifluoroacetic acid (TFA), HCl in dioxane, boron tris(trifluoroacetate) and cyanogen bromide; and reaction in solution with isolation and purification of intermediates are methods well-known to those of ordinary skill in the art. The reaction may be carried out with the peptide either in solution or attached to a solid-phase support. In the solid phase method, the peptide is released from the solid-phase support following completion of the synthesis.

In an embodiment, peptide synthesis method may follow Merrifield solid-phase procedures. See Merrifield, 1963, J. Am. Chem. Soc. 85: 2149-54 and Merrifield, 1965, Science 50: 178-85. Additional information about the solid-phase synthetic procedure can be obtained from the treatises: Atherton & Sheppard, 1989, "Solid Phase Peptide Synthesis: A Practical Approach", Oxford. University Press, NY, N.Y.; Stewart & Young, 1984, "Solid phase peptide synthesis", 2nd edition, Pierce Chemical Company, Rockford, Ill.; and the review chapters by R. Merrifield, 1969, Adv. Enzymol. 32: 221-296, and by B. W. Erickson and R. Merrifield, 1976, in "The Proteins", Vol. 2, pp. 255 et seq., edited by Neurath and Hill, Academic Press, NYC, N.Y. Peptide synthesis may follow synthetic techniques such as those set forth in Fields et al., 2008, "Introduction to Peptide Synthesis", in "Current Protocols in Molecular Biology", Chapter 11, Unit 11.15, John Wiley and Sons, Hoboken, N.J., and Amblard et al., 2006, Molecular Biotechnology 33: 239-254.

The synthesis of peptides by solution methods is described in "The Proteins", 3rd Edition, Vol. 11, Neurath et al., Eds., Academic Press, St. Louis, Mo., 1976. Other general references to the synthesis of peptides include: "Peptide Synthesis Protocols", 1994, edited by M. W. Pennington and Ben M. Dunn, Humana Press, Totowa, N.J.; Bodanszky, 1993, "Principles of Peptide Synthesis", 2nd edition, Springer-Verlag, NYC,N.Y.; Lloyd-Williams et al., 1997, "Chemical Approaches to the Synthesis of Peptides and Proteins", CRC Press, Boca Raton, Fla.; and "Synthetic Peptides: A User's Guide", G. Grant, Ed., Oxford University Press, NY, N.Y., 2002.

In accordance with the present invention, as described above or as discussed in the Examples below, there may be employed conventional chemical and biochemical techniques that are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

The invention is described hereafter with reference to the following examples. The examples are provided for the purpose of illustration only and the invention should in no way be construed as being limited to these examples, but rather should be construed to encompass any and all variations that become evident as a result of the teaching provided herein.

Materials & Methods

NMR spectra were obtained using a Bruker WM-400 (400 MHz $^1$H, 125 MHz $^{13}$C) spectrometer.

HPLC-MS was acquired using a Hewlett-Packard Series 1200 instrument with a Waters Xterra MS $C_{18}$ column (3 µm packing, 4.6×150 mm) with a solvent system of $H_2O$/acetonitrile with 0.1% formic acid at a flow rate of 0.8 mL/min.

Example 1

Generation of Lithium Methyldiphenylsilane (21)

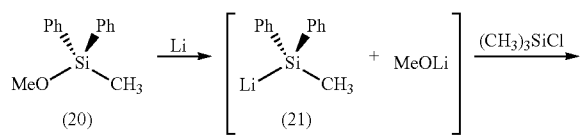

-continued

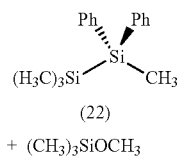

+ (CH$_3$)$_3$SiOCH$_3$

To an excess of lithium shot in THF (4 mL) under argon at 0° C. was added chlorotrimethylsilane (0.1 mL) and the mixture was stirred for 40 minutes. The solution was removed by syringe and replaced with fresh THF (5 mL).

Methoxy(methyl)diphenylsilane (20) (0.34 g, 1.49 mmol) was added and the mixture stirred at 0° C. Aliquots of the mixture were removed after 1.0 hour, 1.5 hours, 2.5 hours and 3.5 hours of reaction time, and added to a flask containing a large excess of chlorotrimethylsilane. The resulting mixture was stirred for 10 minutes, evaporated, and analyzed by $^1$H NMR spectroscopy to monitor the disappearance of (20) and the formation of (22). Based on these spectra, the silyl ether (20) was completely converted to the silyllithium reagent (21) after 3.5 hours.

$^1$H NMR spectrum of (22): (CDCl$_3$) δ 0.16 (s, 9H), 0.61 (s, 3H), 7.34-7.50 (m, 10H).

Example 2

1,1,1-Trimethyl-2-(2-methyl-3-((trimethylsilyl)oxy) propyl)-2,2-diphenyldisilane (25)

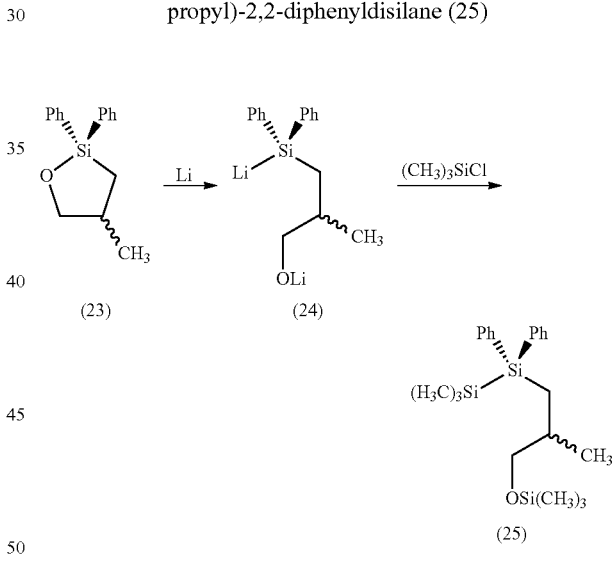

To an excess of lithium shot in THF (4 mL) under argon was added chlorotrimethylsilane (0.1 mL) and the mixture was stirred for 40 minutes. The solution was removed via syringe and replaced by fresh THF (4 mL), followed by racemic silyl ether (23) (0.15 g, 0.58 mM) to give a 0.15 M solution of silane. Aliquots of the solution were removed periodically and quenched with chlorotrimethylsilane, concentrated and examined by $^1$H NMR. After 6 h at room temperature the reaction was complete, showing only product (25).

$^1$H NMR spectrum of (25): (CDCl$_3$) δ 0.06 (s, 9H), 0.17 (s, 9H), 0.78 (d, 3H, J=6.5 Hz), 0.94 (dd, 1H, J=9, 15 Hz), 1.39 (dd, 1H, J=4.5, 15 Hz), 1.82-1.84 (m, 1H), 3.28 (dd, 1H, J=7.3, 9.8 Hz), 3.34 (dd, 1H, J=6, 10 Hz), 7.32-7.51 (m, 10H).

$^{13}$C NMR spectrum of (25): (CDCl$_3$) δ 135.6, 135.5, 128.8, 127.9, 70.4, 32.8, 20.0, 16.9, −0.35, −1.05.

Example 3

N-((R)-1-(((S)-3-Hydroxy-2-methylpropyl)diphenyl-silyl)-3-methlbutyl-2-methylpropane-2-sulfinamide (27) and N-((R)-1-(((R)-3-Hydroxy-2-methylpropyl)diphenyl-silyl)-3-methylbutyl)-2-methylpropane-2-sulfina-mide (28)

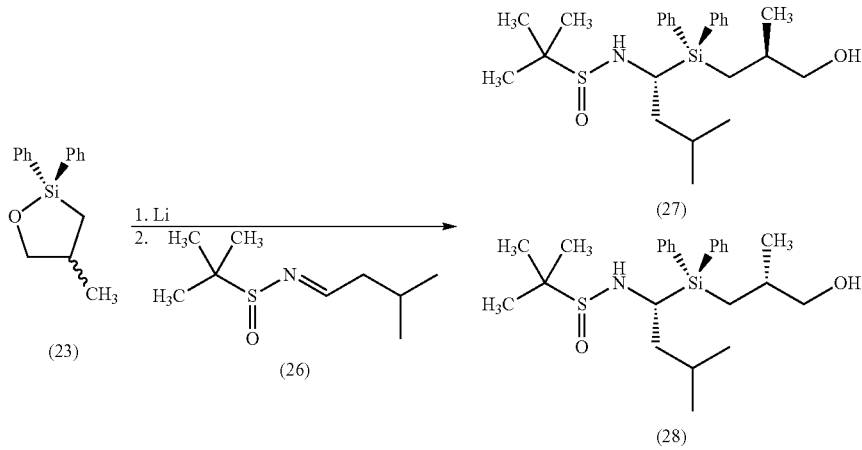

A solution of racemic dianion (24) (0.35 mmol in THF), prepared as described above, was added dropwise to a −78° C. solution of (26) (30 mg, 0.18 mmol) in THF (2.2 mL) and the resulting mixture stirred for 2 h. After addition of saturated ammonium chloride solution the aqueous phase was extracted with ethyl acetate. The combined organics were dried over sodium sulfate, filtered and concentrated. Flash chromatography gave the diastereomeric mixture of (27) and (28) (70%). Rf=0.44 (1:1 ethyl acetate/hexanes).

$^1$H NMR spectrum of the mixture: (CDCl$_3$) δ 0.79-0.82 (m, 3H), 0.87-0.90(m, 3H), 0.95-0.99(m, 3H), 1.036 (s, 4.5H), 1.042 (s, 4.5H), 1.30-1.38(m, 1H), 1.38-1.44(m, 2H), 1.55-1.65(br, 1H), 1.65-1.73(m, 1H), 2.06-2.14(m, 1H), 2.57-2.69 (m, 1H), 3.32-3.34(m, 2H), 3.47-3.52(m, 1H), 7.39-7.63(m, 10H).

$^{13}$C NMR spectrum of the mixture: (CDCl$_3$) δ 16.55, 16.70, 20.06, 20.12, 21.44, 21.48, 23.16, 24.18, 25.14, 30.05, 32.33, 32.37, 42.83, 42.94, 44.31, 56.95, 70.52, 70.59, 128.30, 128.36, 128.43, 130.16, 130.22, 133.34, 133.47, 133.65, 133.75, 135.94, 135.99, 136.04.

LC-MS, retention time=25.09 min. [M+H]$^+$ calculated for this product=446.3; found=446.2.

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed:

1. A process for preparing a compound of formula (15):

wherein:
R$^1$, R$^2$ and R$^3$ are independently selected from the group consisting of H, C$_{1-10}$ alkyl, substituted C$_{1-10}$ alkyl, C$_{1-10}$ alkenyl, substituted C$_{1-10}$ alkenyl, heteroalkyl, heteroalkenyl, heterocyclyl, substituted heterocyclyl, aryl, substituted aryl, aryl-(C$_{1-3}$)alkyl, substituted aryl-(C$_{1-3}$) alkyl, formyl, alkyl-carbonyl, aryl-carbonyl, and heteroaryl-carbonyl; and, R$^4$ and R$^5$ are independently selected from the group consisting of aryl, substituted aryl, heteroaryl and substituted heteroaryl, said process comprising the step of reacting lithium metal with a compound of formula (11):

to form said compound of formula (15).

2. The process of claim 1, wherein said reaction is conducted in a solvent comprising tetrahydrofuran, diethyl ether or 1,4-dioxane.

3. The process of claim 1, wherein said reaction is run at about 0° C.

4. The process of claim 1, wherein $R^2$ and $R^3$ are H.

5. The process of claim 1, wherein $R^1$ is methyl.

6. The process of claim 1, wherein $R^4$ and $R^5$ are phenyl.

7. The process of claim 1, wherein said compound of formula (11) is (S)-4-methyl-2,2-diphenyl-1,2-oxasilolane.

8. A process for preparing a compound of formula (17):

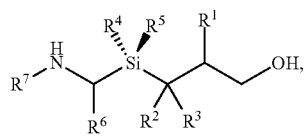

wherein:
- $R^1$, $R^2$ and $R^3$ are independently selected from the group consisting of H, $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, substituted aryl-$(C_{1-3})$alkyl, formyl, alkyl-carbonyl, aryl-carbonyl, and heteroaryl-carbonyl;
- $R^4$ and $R^5$ are independently selected from the group consisting of aryl, substituted aryl, heteroaryl and substituted heteroaryl;
- $R^7$ is —S(O)$R^8$, —S(O)$_2R^8$, —S(O)$_2$NR$^9$R$^{10}$, —C(O)R$^9$, —C(O)NR$^9$R$^{10}$, a protected carboxyl-linked amino acid or a protected carboxyl-linked peptide;
- $R^6$, $R^9$ and $R^{10}$ are independently selected from the group consisting of H, $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, and substituted aryl-$(C_{1-3})$alkyl; and,
- $R^8$ is $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, or substituted aryl-$(C_{1-3})$alkyl;

said process comprising the steps of:
(a) reacting lithium metal with a compound of formula (11):

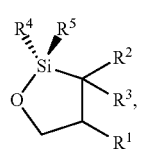

to form a compound of formula (15):

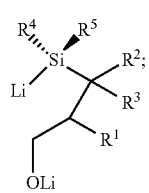

(b) reacting said compound of formula (15) with a compound of formula (16):

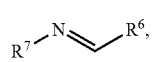

to form a reaction mixture; and,
(c) neutralizing said reaction mixture to form said compound of formula (17).

9. The process of claim 8, wherein said reaction in step (a) is conducted in a solvent comprising tetrahydrofuran, diethyl ether or 1,4-dioxane.

10. The process of claim 8, wherein $R^2$ and $R^3$ are H.

11. The process of claim 8, wherein $R^1$ is methyl.

12. The process of claim 8, wherein $R^4$ and $R^5$ are phenyl.

13. The process of claim 8, wherein said compound of formula (11) is (S)-4-methyl-2,2-diphenyl-1,2-oxasilolane.

14. The process of claim 8, wherein $R^7$ is p-methylphenylsulfinyl.

15. A process for preparing a compound of formula (19):

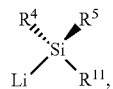

wherein:
- $R^{11}$ is $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, substituted aryl-$(C_{1-3})$alkyl, formyl, alkyl-carbonyl, aryl-carbonyl, or heteroaryl-carbonyl; and,
- $R^4$ and $R^5$ are independently selected from the group consisting of aryl, substituted aryl, heteroaryl and substituted heteroaryl;

said process comprising the step of reacting lithium metal with a compound of formula (18):

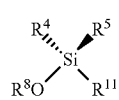

wherein:
- $R^8$ is $C_{1-10}$ alkyl, substituted $C_{1-10}$ alkyl, $C_{1-10}$ alkenyl, substituted $C_{1-10}$ alkenyl, heteroalkyl, heteroalkenyl, heterocyclyl, substituted heterocyclyl, aryl, substituted aryl, aryl-$(C_{1-3})$alkyl, substituted aryl-$(C_{1-3})$alkyl, formyl, alkyl-carbonyl, aryl-carbonyl, or heteroaryl-carbonyl;

to form a solution of said compound of formula (19).

16. The process of claim 15, wherein said reaction is conducted in a solvent comprising tetrahydrofuran, diethyl ether or 1,4-dioxane.

17. The process of claim 15, wherein said reaction is run at about 0° C.

18. The process of claim 15, wherein $R^{11}$ is methyl.

19. The process of claim 15, wherein $R^4$ and $R^5$ are phenyl.

20. The process of claim 15, wherein said compound of formula (18) is methoxy(methyl)diphenylsilane.

* * * * *